United States Patent [19]

Isaac et al.

[11] 4,004,911
[45] Jan. 25, 1977

[54] TRIHYDRIC ALCOHOL DERIVATIVES

[75] Inventors: Eirlys R. Isaac, Sittingbourne; Michael D. Barker, Maidstone, both of England

[73] Assignee: Shell Oil Company, Houston, Tex.

[22] Filed: Apr. 18, 1975

[21] Appl. No.: 569,514

Related U.S. Application Data

[60] Division of Ser. No. 392,394, Aug. 8, 1973, Pat. No. 3,919,251, which is a continuation of Ser. No. 74,505, Sept. 22, 1970, abandoned.

[30] Foreign Application Priority Data

Sept. 23, 1969 United Kingdom ............ 46745/69

[52] U.S. Cl. .................................................. 71/88
[51] Int. Cl.$^2$ ............................................ A01N 9/24

[58] Field of Search ........................................ 71/88

[56] References Cited

UNITED STATES PATENTS

| | | | |
|---|---|---|---|
| 3,344,148 | 9/1967 | Dietrich et al. ................... | 71/88 X |
| 3,427,147 | 2/1969 | Dietrich et al. ........................ | 71/88 |
| 3,644,422 | 2/1972 | Mine et al. ......................... | 71/88 X |
| 3,753,678 | 8/1973 | Young et al. ................... | 260/340.7 |

Primary Examiner—Lewis Gotts
Assistant Examiner—Catherine L. Mills

[57] ABSTRACT

Certain novel trihydric alcohol derivatives, useful as herbicides and fungicides.

7 Claims, No Drawings

TRIHYDRIC ALCOHOL DERIVATIVES

This is a division of application Ser. No. 392,394, filed Aug. 8, 1973 now U.S. Pat. No. 3,919,251, issued Nov. 11, 1975, which is a continuation of Ser. No. 74,505 filed Sept. 22, 1970 now abandoned.

BACKGROUND OF THE INVENTION

1. Field of the Invention

This invention relates to a novel class of trihydric alcohol derivates containing ether and/or ester functions, which possess high herbicidal and fungicidal activity.

2 Description of the Prior Art

A search of the prior art indicates the herbicidal and fungicidal trihydric alcohol derivatives within the scope of this invention to be novel.

SUMMARY OF THE INVENTION

A new series of trihydric alcohol derivatives being at least partially etherified and/or esterified and wherein the three oxy (—O—) oxygen atoms of the alcohol chain are bonded to different carbon atoms, the carbon atom to which the central oxygen atom is attached being tertiary in character have been discovered. These novel compounds have shown high herbicidal activity in the control of certain economically important grass weed species and have proven effective in the control of certain fungal diseases.

This invention, accordingly, is a new series of trihydric alcohol derivatives being at least partially etherified and/or esterified and wherein the three oxy (—O—) oxygen atoms of the alcohol chain are bonded to different carbon atoms, the carbon atom to which the central oxygen atom is attached being tertiary in character, their use as herbicides and fungicides, and pesticidal formulations containing them.

DESCRIPTION OF THE PREFERRED EMBODIMENTS

The novel compounds of this invention can be described by the general formula:

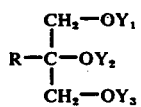
(I)

wherein R represents an alkyl group of 1-6 carbon atoms, suitably methyl, ethyl, propyl or hexyl; and $Y_1$ and $Y_2$ together represent an optionally substituted methylene group of the formula:

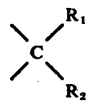
(II)

wherein $R_1$ and $R_2$ each individually represents a hydrogen atom, an optionally substituted alkyl group particularly methyl, benzyl, ethyl, phenylethyl or butyl, a phenyl group optionally substituted by one or more halogen, especially chlorine atoms or by an alkyl group, for example methyl, or $R_1$ and $R_2$ together represent a polymethylene group, particularly tetramethylene, pentamethylene or hexamethylene; and $Y_3$ represents an and aryl group, particularly phenyl, an aralkyl group, particularly a benzyl group optionally substituted in the benzene ring by one or more fluorine or chlorine atoms or by a methyl or phenyl group.

By reason of their high level of biological activity the following compounds are particularly preferred:
 4-benzyloxymethyl-2,2-dimethyl-4-n-propyl-1,3-dioxolane
 4-benzyloxymethyl-2,2-dimethyl-4-ethyl-1,3-dioxolane
 4-benzyloxymethyl-4-methyl-1,3-dioxolane-2-spirocyclohexane It will be appreciated that many of the 2-alkyl glycerol derivatives of the invention may exhibit geometrical and/or optical isomerism. The individual isomers of these compounds together with isomeric mixtures thereof are included within the scope of the present invention. The compounds of formula II are prepared by reacting the corresponding diol with a carbonyl compound of the formula:

(V)

or an acetal or ketal derived from such a carbonyl compound, in the presence of an acid, suitably an inorganic acid such as hydrochloric acid or an arylsulphonic acid such as p-toluene sulphonic acid. The reaction is preferably carried out in an aromatic hydrocarbon, for example benzene or toluene, as solvent.

As mentioned above the trihydric alcohol derivatives of the invention exhibit herbicidal and plant growth regulant properties and the invention therefore includes biologically active compositions comprising a carrier or a surface active agent, or both a carrier and a surface active agent, and as activeingredient at least one trihydric alcohol derivative of the invention.

The term "carrier" as used herein means a material, which may be inorganic or organic and of synthetic or natural origin, with which the active compound is mixed or formulated to facilitate its application to the plant seed, soil or other object to be treated, or its storage, transport or handling. The carrier may be a solid or a fluid. Any of the material usually applied in formulating pesticides may be used as carrier.

Suitable solid carriers are natural and synthetic clays and silicates, for example natural silicas such as diatomaceous earths; magnesium silicates, for example, talcs; magnesium aluminum silicates, for example, attapulgites and vermiculites; aluminum silicates, for example, kaolinites, montmorillinites and micas; calcium carbonates; calcium sulphate; synthetic hydrated silicon oxides and synthetic calcium or aluminum silicates; elements such as for example, carbon and sulphur; natural and synthetic resins such as for example coumarone resins, polyvinyl chloride and styrene polymers and copolymers; solid polychlorophenols; bitumen; waxes such as for example, beeswax, paraffin wax, and chlorinated mineral waxes; solid fertilizers, for example superphosphates.

Examples of suitable fluid carriers are water, alcohols, such as, for example, isopropanol, glycols; ketones, such as for example, acetone, methyl ethyl ketone, methyl isobutyl ketone and cyclohexanone; ethers; aromatic hydrocarbons such as, for example, benzene, toluene and xylene; petroleum fractions such as, for example, kerosene, light mineral oils; chlorinated hydrocarbons such as, for example, carbon tetrachloride, perchloroethylene, trichloroethane, including liquefied normally vaporous gaseous compounds. Mixtures of different liquids are often suitable.

The surface-active agent may be an emulsifying agent or a dispersing agent or a wetting agent; it may be nonionic or ionic. Any of the surface-active agents usually applied in formulating herbicides or insecticides may be used. Examples of suitable surface-active agents are the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example, sodium lauryl sulphate, sodium secondary alkyl sulphates, sodium salts of sulphonated castor oil, and sodium alkylaryl sulphonates such as sodium dodecylbenzene sulphonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates and aerosols. Wettable powders are usually compounded to contain 25, 50 or 75% w of toxicant and usually contain, in addition to solid carrier, 3–10% w of a dispersing agent and, where necessary, 0–10% w of stabilizer(s) and/or additives such as penetrants or stickers. Dusts are usually formulated as a dust concentrate having a similar composition to that of a wettable powder but without a dispersant, and are diluted in the filed with further solid carrier to give a composition usually containing ½–10% w of toxicant. Granules are usually prepared to have a size between 10 and 100 BS mesh, and may be manufactured by agglomeration or impregnation techniques. Generally, granules will contain ½–25% w toxicant and 0–10% w of additives such as stabilizers, slow release modifiers and binding agents. Emulsifiable concentrates usually contain, in addition to the solvent and, when necessary, co-solvent, 10–50% w/v toxicant, 2–20% w/v emulsifiers and 0–20% w/v of appropriate additives such as stabilers, penetrants and corrosion inhibitors. Suspension concentrates are compounded so as to obtain a stable, non-sedimenting, flowable product and usually contain 10–75% w toxicant, 0.5–15% w dispersing agents, 0.1–10% w of suspending agents such as protective colloids and thixotropic agents, 0–10% w of appropriate additives such as defoamers, corrosion inhibitors, stabilizers, penetrants and stickers, and as carrier, water or an organic liquid in which the toxicant is substantially insoluble; certain organic solids or inorganic salts may be dissolved in the carrier to assist in preventing sedimentation or as antifreeze agents for water.

The compositions of the invention may contain other ingredients, for example, protective colloids such as gelatin, glue, casein, gums, cellulose ethers, and polyvinyl alcohol; thixotropic agents, e.g., bentonites, sodium polyphosphates; stabilizers such as ethylene diamine tetra-acetic acids, urea, triphenyl phosphate; and stickers, for example non-volatile oils.

Aqueous dispersion and emulsions, for example, compositions obtained by diluting a wettable powder or an emulsifiable concentrate according to the invention with water, also lie within the scope of the present invention. The said emulsions may be of the water-in-oil or of the oil-in-water type, and may have a thick "mayonnaise"-like consistency.

The trihydric alcohol derivatives of the present invention are of interest as herbicides and particularly as selective herbicides for pre-emergence application to control grass weeds. The invention includes therefore within its scope a method of protecting crops at a locus from competition by grass weeds which comprises applying to the locus a trihydric alcohol derivative or composition of the invention.

The compounds of the invention may be used in admixture with other herbicides and pesticides. In particular they may be mixed with active materials possessing pre-emergence activity against broad-leaf weeds to give herbicide combinations exhibiting broad-spectrum pre-emergence activity. Examples of such active materials are s-triazine derivatives such as 2,4-bis(isopropylamino)-6-methylthio-s-triazine, or 2-chloro-4-ethylamino-6-isopropylamino-s-triazine, pyridazole derivatives such as 5-amino-4-chloro-2-phenyl-pyridaz-3-one, or 1,4-naphthaquinone derivatives.

The invention is further illustrated in the following Examples:

EXAMPLE I
4-Benzyloxymethyl-2,2,4-trimethyl-1,3-dioxolane a. preparation of 2-methylglycerol

Methallyl alcohol (20.0g), alumina (20.0g) and tungstic acid (2.0g) in water (100 ml) were heated to 60° C and then hydrogen peroxide (31.6 ml of 30 w/v solution) was slowly added. During the addition the temperature of the mixture was maintained at 60° C by cooling. When the addition was complete the mixture was maintained at 60° C for a further hour and then at 95° C for 2 hours. After cooling the mixture was filtered and the filtrate passed through two columns containing respectively Amberlite IRA 400 and Permutit Zeo-Carb. 225. The solvent was then removed from the solution to give the crude 2-methylglycerol which was not purified further.

b. Preparation of 4-hydroxymethyl-2,2,4-trimethyl-1,3-dioxolane

2-Methylglycerol (50 g, prepared as in (a)), acetone (150 ml), p-toluene sulphonic acid (1.5g) and petroleum ether (150 ml, b.p. (40°–60° C) were heated together for 24 hours at reflux temperature under two Vigreux columns (40 cm length each) and a Dean and Stark trap for removal of water. The reaction mixture was cooled and fused sodium acetate (1.5g) was added. The suspension was stirred at room temperature for 30 minutes and then filtered. The solvents were removed from the filtrate under reduced pressure and the residue was fractionally distilled. 4-hydroxymethyl-2,2,4-trimethyl-1,3-dioxolane was obtained as a colorless liquid having a b.p. 77° C at 12 mm Hg.

Preparation of 4-benzyloxymethyl-2,2,4-trimethyl-1,3-dioxolane

4-Hydroxymethyl-2,2,4-trimethyl-1,3-dioxolane (10g, prepared as in (b)) was added dropwise to a stirred suspension of sodium hydride (3g, 50% dispersion in oil) in dry toluene (150 ml). When the addition was complete the solution was heated under reflux until no more hydrogen was evolved. Benzyl chloride (7.85g) was added to the refluxing solution over a period of 15 minutes, after which the solution was heated under reflux for a further 3 hours. The solution was then cooled, washed with water (3 × 30 ml), dried and the solvent removed under reduced pressure. The residual oil was fractionally distilled to give the desired product as a colorless liquid having a b.p. 80° C at 0.2 mm Hg.

Analysis
Calculated for $C_{14}H_{20}O_3$: C 71.3; H 8.5%
Found: C 71.3; H 8.7%

EXAMPLE II hydride (5.25g) in aqueous methanol (45 ml) at 30°–40° C. When the reduction was complete, aqueous sodium hydroxide (120 ml of 13% solution) was added and the mixture heated at 80° C for 1 hour. The solution was cooled and extracted with ether. The dried extracts were evaporated and the residual oil was dried with magnesium sulphate and fractionally distilled to yield 2-methylenepentan-1-ol having a b.p. 61°–63° C at 15 mm Hg.

b. Following a series of reactions similar to those of Example I (a) - (c) but using 2-methylenepentan-1-ol as starting material, the desired product was obtained as a colorless liquid having a b.p. 97° C at 0.3 mm Hg.

Analysis
Calculated for $C_{16}H_{24}O_3$: C 72.7; H 9.1%
Found: C 72.4; H 9.2%

EXAMPLE III

Following procedures similar to those of Examples I and II further compounds were prepared, whose physical characteristics and analyses are given in Table 1.

Table 1

| Compound | Boiling Point ° C/mmHg | Analysis | |
|---|---|---|---|
| 4-benzyloxymethyl-4-n-hexyl-2,2-dimethyl-1,3-dioxolane | 124/0.3 | Calculated for $C_{19}H_{30}O_3$: Found: | C 74.5; H 9.8% C 74.5; H 9.9% |
| 4-(4'-chlorobenzyloxymethyl)-2,2,4-trimethyl-1,3-dioxolane | 94/0.1 | Calculated for $C_{14}H_{19}O_3Cl$: Found: | C 62.0; H 7.0% C 62.3; H 7.2% |
| 4-(4'-methylbenzyloxymethyl)-2,2,4-trimethyl-1,3-dioxolane | 91/0.3 | Calculated for $C_{15}H_{22}O_3$: Found: | C 72.0; H 8.8% C 71.6; H 8.8% |
| 4-(3'-methylbenzyloxymethyl)-2,2,4-trimethyl-1,3-dioxolane | 90/0.3 | Calculated for $C_{15}H_{22}O_3$: Found: | C 72.0; H 8.8% C 72.0; H 8.6% |
| 4-(3',4'-dichlorobenzyloxymethyl)-2,2,4-trimethyl-1,3-dioxolane | 121/0.3 | Calculated for $C_{14}H_{18}O_3Cl_2$: Found: | C 55.1; H 5.9% C 55.9; H 6.0% |
| 4-benzyloxymethyl-4-ethyl-2,2-dimethyl-1,3-dioxolane | 96/0.3 | Calculated for $C_{15}H_{22}O_3$: Found: | C 72.0; H 8.8% C 72.2; H 9.0% |
| 4-benzyloxymethyl-4-isopropyl-2,2-dimethyl-1,3-dioxolane | 99/0.4 | Calculated for $C_{16}H_{24}O_3$: Found: | C 72.7; H 9.1% C 72.9; H 9.0% |
| 4-benzyloxymethyl-2-isobutyl-2,4-dimethyl-1,3-dioxolane | 103/0.3 | Calculated for $C_{17}H_{26}O_3$: Found: | C 73.4; H 9.4% C 73.3; H 9.4% |
| 4-benzyloxymethyl-2-ethyl-2,4 dimethyl-1,3-dioxolane | 98/0.5 | Calculated for $C_{15}H_{22}O_3$: Found: | C 72.0; H 8.8% C 72.9; H 9.1% |
| 4-allyloxymethyl-2,2,4-trimethyl-1,3-dioxolane | 70/12 | Calculated for $C_{10}H_{18}O_3$: Found: | C 64.6; H 9.7% C 65.0; H 9.9% |
| 4-benzyloxymethyl-2,4-dimethyl-2-phenyl-1,3-dioxolane | 125/0.15 | Calculated for $C_{19}H_{22}O_3$: Found: | C 76.5; H 7.4% C 76.7; H 7.7% |
| 4-(4'-fluorobenzyloxymethyl)-2,2,4-trimethyl-1,3-dioxolane | 83/0.3 | Calculated for $C_{14}H_{19}O_3F$: Found: | C 66.1; H 7.5% C 66.3; H 7.8% |
| 4-benzyloxymethyl-2,2-diphenyl-4-methyl-1,3-dioxolane | m.p. 54–56° C | Calculated for $C_{24}H_{24}O_3$: Found: | C 80.0; H 6.7% C 80.1; H 6.5% |
| 4-(biphenyl-4'-yl methoxy methyl)-2,2,4-trimethyl-1,3-dioxolane | 142/0.15 | Calculated for $C_{20}H_{24}O_3$: Found: | C 76.9; H 7.7% C 76.7; H 8.0% |
| 4-(2',3',6'-trichlorobenzyloxymethyl)-2,2,4-trimethyl-1,3-dioxolane | 132–138 /0.4 | Calculated for $C_{14}H_{17}O_3Cl_3$: Found: | C 49.4; H 5.0% C 49.0; H 5.1% |
| 4-benzyloxymethyl-4-methyl-2-phenyl-1,3-dioxolane | 136/0.15 | Calculated for $C_{18}H_{20}O_3$: Found: | C 76.1; H 7.0% C 76.4; H 7.4% |

4-Benzyloxymethyl-2,2-dimethyl-4-n-propyl-1,3-dioxolane a. Preparation of 2-n-propylglycerol Formaldehyde (50 ml of 37–41% w solution) and dimethylamine hydrochloride (53g) were mixed to give a clear solution, to which was added slowly valericaldehyde (50g). The solution was maintained at 55° C for 1 hour and then at 70° C for 22–24 hours. The crude product was separated by steam distillation, dissolved in methanol (100 ml) and reduced with sodium boro-

EXAMPLE IV

3-Benzyloxymethyl-4-methyl-2-p-tolyl-1,3-dioxolane

3-Benzyloxy-2-methylpropane-1,2-diol (6.5g), p-tolualdehyde (4.0g) and p-toluenesulphonic acid in benzene (200 ml) were heated together under reflux until no more water was liberated. The cooled solution was washed first with 5% potassium carbonate solution and the water. The solution was then dried and the solvent removed under reduced pressure. The residual liquid was purified by chromatography on alumina using benzene as eluant to yield the desired product ($n_d^{26}$ 1.5361).

| Analysis | |
|---|---|
| Calculated for $C_{19}H_{22}O_3$: | C 76.5; H 7.4% |
| Found: | C 76.6; H 7.5% |

EXAMPLE V

Following a procedure similar to that given in the previous Example, further compounds were prepared whose physical characteristics and analyses are set out in Table 2.

Table 2

| Compound | b.p.° C/mmHg or $n_D$ | Analysis | |
|---|---|---|---|
| 4-benzyloxymethyl-2-(4-chorophenyl)-4-methyl-1,3-dioxolane | $n_D^{26.5}$ 1.5482 | Calculated for $C_{18}H_{19}O_3Cl$ Found | C 67.8; H 5.9% C 68.0; H 6.3% |
| 4-benzyloxymethyl-4-methyl-1,3-dioxolane-2-spirocyclohexane | .102/0.15 | Calculated for $C_{17}H_{24}O_3$ Found | C 74.0; H 8.7% C 74.4; H 8.9% |
| 4-benzyloxymethyl-2-benzyl-2,4-dimethyl-1,3-dioxolane | 130/0.1 | Calculated for $C_{20}H_{24}O_3$ Found | C 77.0; H 7.7% C 77.2; H 7.9% |
| 4-benzyloxymethyl-4-methyl-1,3-dioxolane-2-spirocyclopentane | 107/0.2 | Calculated for $C_{16}H_{22}O_3$ Found | C 73.4; H 8.4% C 73.4; H 8.4% |
| 4-benzyloxymethyl-4-methyl-2-(2-phenylethyl)-1,3-dioxolane | 151/0.1 | Calculated for $C_{20}H_{24}O_3$ Found | C 77.0; H 7.7% C 76.7; H 7.8% |
| 4-benzyloxymethyl-4-methyl-1,3-dioxolane | $n_D^{27}$ 1.5008 | Calculated for $C_{12}H_{16}O_3$ Found | C 69.2; H 7.7% C 69.6; H 7.7% |
| 4-benzyloxymethyl-4-methyl-1,3-dioxolane-2-spirocycloheptane | $n_D^{27}$ 1.5069 | Calculated for $C_{18}H_{26}O_3$ Found | C 74.5; H 9.0% C 74.1; H 9.1% |

EXAMPLE VI

4-Benzyloxymethyl-2,4-dimethyl-1,3-dioxolane

3-Benzyloxy-2-methylpropane-1,2-diol (5.0g), 1,1-diethoxyethane (3.0g) and p-toluenesulphonic acid were heated at 110°–115° C with stirring until no more alcohol was evolved. The mixture was then heated at 140°–145° C for 15 minutes. After cooling, the mixture was dissolved in ether and the resulting solution was then washed with 5% potassium carbonate solution followed by water. The solution was dried over anhydrous magnesium sulphate and the solvent was removed under reduced pressure to yield a liquid which on distillation gave the desired product having a b.p. 81°–82° C at 0.3 mm Hg.

| Analysis | |
|---|---|
| Calculated for $C_{13}H_{18}O_3$: | C 70.3; H 8.1% |
| Found: | O 70.6; H 8.0% |

EXAMPLE VII

Following a procedure similar to that of Example VI the following compounds were also prepared;
4-benzyloxymethyl-2-benzyl-4-methyl-1,3-dioxolane b.p. 134° C at 0.2 mm Hg.

| Analysis | |
|---|---|
| Calculated for $C_{19}H_{22}O_3$: | C 76.6; H 7.4% |
| Found: | C 77.0; H 7.4% |

EXAMPLE VIII

4-Phenoxymethyl-2,2,4-trimethyl-1,3-dioxolane

4-Chloromethyl-2,2,4-trimethyl-1,3-dioxolane (5.0g) and sodium phenoxide (3.7g, prepared from phenol and sodium hydride) in dimethyl sulphoxide (90 ml) were heated together at 140° C for 4 hours. The reaction mixture was diluted with water and the aqueous solution extracted with ether. The ether extracts were dried and the solvent was removed under reduced pressure to yield a liquid which, on distillation, gave the desired product having a b.p. 83.5° C at 0.3 mm Hg.

EXAMPLE IX

Following a procedure similar to that of Example IX, the following compounds were also prepared:
4-methyl-4-phenoxymethyl-2-phenyl-1,3-dioxolane ($n_D^{27}$ 1.5393)

| Analysis | |
|---|---|
| Calculated for $C_{17}H_{18}O_3$: | C 75.6; H 6.7% |
| Found: | C 75.8; H 6.9% |

EXAMPLE X

Herbicidal Activity

To evaluate their herbicidal activity, the compounds of the invention were tested using as a representative range of plants: maize, *Zea mays* (Mz); oat, *Avena sativa* (O); rye grass, *Lolium perenne* (RG); pea, *Pisum sativum* (P); linseed, *Linum usitatissium* (L); mustard, *Sinapis alba* (M); and sugar beet, *Beta vulgaris* (SB).

The tests fall into two categories, pre-emergence and post-emergence. The pre-emergence tests involved spraying a liquid formulation of the compound onto the soil in which the seeds of the plant species mentioned above had recently been sown. The post-emergence tests involved two types of test, viz, soil drench and foliar spray tests. In the soil drench tests the soil in which seedling plants of the above species were growing was drenched with a liquid formulation containing a compound of the invention, and in the foliar spray tests the seedling plants were sprayed with such a formulation.

The soil used in the tests was a steam-sterilized, modified John Innes Compost mixture in which half the peat, by loose bulk, had been replaced by vermiculite.

The formulations used in the tests were prepared by diluting with water and solutions of the compounds in acetone containing 0.4% by weight of an alkylphenol-/ethylene oxide condensate available under the trade name Triton X-155. In the soil spray and foliar spray tests the acetone solutions were diluted with an equal volume of water and the resulting formulations applied at two dosage levels corresponding to 11.2 and 1.1 pounds of active material per acre, respectively. In the soil drench tests one volume of the acetone solution was diluted to 155 volumes with water and the resulting formulation applied at one dosage level equivalent to 11.2 pounds of active material per acre.

In the pre-emergence tests untreated sown soil and in the post-emergence tests untreated soil bearing seedling plants were used as controls.

The herbicidal effects of the compounds were assessed visually seven days after spraying the foliage and drenching the soil and eleven days after spraying the soil, and were recorded on a 0–9 scale. A rating 0 indicates no effect on the treated plants, a rating 2 indicates a reduction in fresh weight of stem and leaf of the plants of approximately 25%, a rating 5 indicates a reduction of approximately 55%, a rating 9 indicates a reduction of 95% etc.

The results of the tests are set out in Table 3.

In the tests on certain of the compounds oat was replaced by rice, Oryza sativa (R) and rye grass was replaced by barnyard grass, Echinochloa crusgalli (BG). The results of these tests are given in Table 4.

Table 3

| Compound | Dosage lb/A | Post-Emergence (Plants) | | | | | | | | | | | | | Pre-Emergence (Seeds) | | | | | | |
|---|---|---|---|---|---|---|---|---|---|---|---|---|---|---|---|---|---|---|---|---|---|
| | | Soil Drench | | | | | | | Foliar Spray | | | | | | Soil Spray | | | | | | |
| | | Mz | O | RG | P | L | M | SB | Mz | O | RG | P | L | M | SB | Mz | O | RG | P | L | H | SB |
| 4-benzyloxymethyl-2,2,4-trimethyl 1,3-dioxolane | 11.2 | 5 | 5 | 5 | 2 | 7 | 0 | 3 | 4 | 4 | 2 | 0 | 8 | 8 | 1 | 9 | 9 | 9 | 8 | 7 | 2 | 0 |
| | 1.1 | | | | | | | | 0 | 0 | 0 | — | 0 | 0 | 0 | 5 | 7 | 9 | 2 | 4 | 0 | — |
| 4-(4'chlorobenzyloxy-methyl)-2,2,4-trimethyl-1,3-dioxolane | 11.2 | 4 | 0 | 0 | 0 | 0 | 0 | 0 | 1 | 4 | 1 | 2 | 8 | 9 | 9 | 5 | 0 | 8 | 0 | 0 | 0 | 0 |
| | 1.1 | | | | | | | | 1 | 0 | 0 | 0 | 1 | 4 | 0 | 2 | — | 0 | — | — | — | — |
| 4-benzyloxymethyl-4-n-propyl-2,2-dimethyl-1,3-dioxolane | 11.2 | 8 | 6 | 6 | 0 | 5 | 0 | 0 | 8 | 6 | 5 | 4 | 8 | 9 | 8 | 9 | 9 | 9 | 8 | 5 | 1 | 0 |
| | 1.1 | | | | | | | | 1 | 0 | 0 | 0 | 1 | 1 | 0 | 7 | 5 | 9 | 5 | 4 | 0 | 0 |
| 4-benzyloxymethyl-2-isobutyl-2,4-dimethyl-1,3-dioxolane | 11.2 | 7 | 5 | 5 | 0 | 0 | 0 | 0 | 9 | 5 | 5 | 0 | 7 | 8 | 4 | 9 | 9 | 9 | 6 | 4 | 2 | 0 |
| | 1.1 | | | | | | | | 3 | 0 | 0 | — | 0 | 0 | 0 | 3 | 2 | 8 | 0 | 0 | 0 | — |
| 4-(4'-methylbenzyloxy-methyl)-2,2,4-trimethyl-1,3-dioxolane | 11.2 | 2 | 0 | 0 | 0 | 3 | 0 | 0 | 2 | 1 | 1 | 6 | 7 | 9 | 8 | 0 | 0 | 2 | 0 | 0 | 0 | 0 |
| | 1.1 | | | | | | | | 1 | 0 | 0 | 0 | 1 | 2 | 0 | — | — | 0 | — | — | — | — |
| 4-(3'methylbenzyloxy-methyl)-2,2,4-trimethyl-1,3-dioxolane | 11.2 | 3 | 0 | 0 | 0 | 0 | 0 | 0 | 3 | 2 | 1 | 3 | 7 | 9 | 8 | 0 | 0 | 4 | 0 | 0 | 0 | 0 |
| | 1.1 | | | | | | | | 0 | 0 | 0 | 0 | 1 | 1 | 0 | — | — | 0 | — | — | — | — |
| 4-(3',4'-dichlorobenzyloxy-methyl)-2,2,4-trimethyl-1,3-dioxolane | 11.2 | 0 | 0 | 0 | 0 | 0 | 0 | 0 | 2 | 7 | 1 | 3 | 7 | 9 | 9 | 0 | 0 | 4 | 0 | 0 | 0 | 0 |
| | 1.1 | | | | | | | | 0 | 0 | 0 | 0 | 1 | 2 | 4 | — | — | 0 | — | — | — | — |
| 4-benzyloxymethyl-4-ethyl-2,2-dimethyl-1,3-dioxolane | 11.2 | 8 | 5 | 4 | 0 | 5 | 4 | 2 | 8 | 5 | 7 | 3 | 6 | 7 | 9 | 9 | 9 | 9 | 8 | 6 | 7 | 0 |
| | 1.1 | | | | | | | | 6 | 1 | 3 | 1 | 3 | 2 | 4 | 7 | 7 | 9 | 5 | 4 | 0 | — |
| 4-benzyloxymethyl-4-methyl-2-phenyl 1,3-dioxolane | 11.2 | 7 | 7 | 7 | 0 | 4 | 2 | 0 | 6 | 6 | 4 | 1 | 7 | 8 | 7 | 4 | 6 | 9 | 0 | 7 | 2 | 2 |
| | 1.1 | | | | | | | | 3 | 0 | 0 | 0 | 2 | 3 | 0 | 6 | 4 | 9 | — | 5 | 0 | 0 |
| 4-benzyloxymethyl-2-ethyl-2,4-dimethyl-1,3-dioxolane | 11.2 | 7 | 5 | 5 | 0 | 4 | 1 | 0 | 8 | 6 | 5 | 2 | 7 | 9 | 8 | 9 | 9 | 9 | 2 | 2 | 2 | 0 |
| | 1.1 | | | | | | | | 0 | 0 | 0 | 0 | 0 | 0 | 0 | 5 | 4 | 8 | 0 | 0 | 0 | — |
| 4-benzyloxymethyl-2,4-dimethyl-2-phenyl-1,3-dioxolane | 11.2 | 5 | 2 | 5 | 0 | 0 | 0 | 0 | 3 | 6 | 4 | 2 | 6 | 5 | 6 | 9 | 4 | 7 | 7 | 4 | 2 | 0 |
| | 1.1 | | | | | | | | 0 | 2 | 0 | 0 | 0 | 0 | 0 | 0 | 0 | 6 | 0 | 0 | 0 | — |

Table 4

| Compound | Dosage lb/A | Post-Emergence (Plants) | | | | | | | | | | | | | Pre-Emergence (Seeds) | | | | | | |
|---|---|---|---|---|---|---|---|---|---|---|---|---|---|---|---|---|---|---|---|---|---|
| | | Soil Drench | | | | | | | Foliar Spray | | | | | | Soil Spray | | | | | | |
| | | Mz | R | BG | P | L | M | SB | Mz | R | BG | P | L | M | SB | Mz | R | BG | P | L | M | SB |
| 4-(4'-fluoro benzyloxy-methyl)-2,2,4-trimethyl-1,3-dioxolane | 11.2 | 6 | 6 | 7 | 0 | 4 | 0 | 0 | 6 | 3 | 7 | 1 | 6 | 9 | 6 | 9 | 9 | 9 | 7 | 4 | 0 | 0 |
| | 1.1 | | | | | | | | | | | | | | | 0 | 7 | 6 | 2 | 0 | — | — |
| 4-benzyloxymethyl-2,2,4-trimethyl-1,3-dioxolane | 11.2 | 0 | 0 | 0 | 0 | 0 | 0 | 0 | 1 | 3 | 5 | 2 | 6 | 7 | 3 | 0 | 0 | 0 | 0 | 0 | 0 | 0 |
| | 1.1 | | | | | | | | | | | | | | | — | — | — | — | — | — | — |
| 4-(4'-phenylbenzyloxy-methyl)-2,2,4-trimethyl-1,3-dioxolane | 11.2 | 0 | 0 | 0 | 0 | 0 | 0 | 0 | 3 | 4 | 6 | 3 | 6 | 9 | 5 | 0 | 0 | 0 | 0 | 0 | 0 | 0 |
| | 1.1 | | | | | | | | 1 | 1 | 2 | 0 | 2 | 9 | 2 | — | — | — | — | — | — | — |
| 4-phenoxymethyl-2,2,4-trimethyl-1,3-dioxolane | 11.2 | 5 | 0 | 4 | 0 | 2 | 0 | 0 | 4 | 3 | 5 | 2 | 5 | 9 | 3 | 3 | 6 | 9 | 3 | 4 | 0 | 0 |
| | 1.1 | | | | | | | | 0 | 1 | 0 | 0 | 0 | 0 | 0 | 0 | 0 | 0 | 0 | 0 | — | — |

Table 4-continued

| Compound | Dosage lb/A | Post-Emergence (Plants) Soil Drench | | | | | | | Foliar Spray | | | | | | | Pre-Emergence (Seeds) Soil Spray | | | | | |
|---|---|---|---|---|---|---|---|---|---|---|---|---|---|---|---|---|---|---|---|---|---|
| | | Mz | R | BG | P | L | M | SB | Mz | R | BG | P | L | M | SB | Mz | R | BG | P | L | M | SB |
| 4-(2',3',6',-trichloro-benzyloxymethyl 2,2,4-trimethyl-1,3-dioxolane | 11.2 | 1 | 0 | 0 | 0 | 0 | 0 | 0 | 0 | 1 | 8 | 1 | 5 | 8 | 9 | 6 | 7 | 9 | 7 | 3 | 0 | 0 |
| | 1.1 | | | | | | | | — | 0 | 0 | 0 | 0 | 0 | 1 | 3 | 0 | 9 | 0 | 0 | — | — |
| 4-benzyloxymethyl-2-benzyl-2-methyl-1,3,-dioxolane | 11.2 | 1 | 7 | 6 | 0 | 0 | 0 | 0 | 4 | 1 | 9 | 0 | 4 | 3 | 2 | 6 | 3 | 9 | 6 | 4 | 0 | 0 |
| | 1.1 | | | | | | | | 0 | 0 | 3 | 0 | 0 | 0 | 0 | 1 | 0 | 9 | 0 | 0 | — | — |
| 4-benzyloxymethyl-4-methyl-2-p-tolyl-1,3-dioxolane | 11.2 | 3 | 0 | 4 | 0 | 0 | 0 | 0 | 0 | 1 | 7 | 0 | 3 | 6 | 3 | 8 | 9 | 9 | 2 | 3 | 0 | 0 |
| | 1.1 | | | | | | | | — | 0 | 0 | 0 | 0 | 0 | 0 | 0 | 4 | 9 | 0 | 0 | — | — |
| 4-benzyloxymethyl-2-(4-chlorophenyl)-4-methyl-1,3-dioxolane | 11.2 | 0 | 0 | 1 | 0 | 0 | 0 | 0 | 1 | 2 | 7 | 0 | 3 | 7 | 2 | 4 | 6 | 9 | 0 | 0 | 0 | 0 |
| | 1.1 | | | | | | | | 0 | 0 | 0 | — | 0 | 0 | 0 | 0 | 1 | 7 | — | — | — | — |
| 4-benzyloxymethy-4-methyl-1,3,-dioxolane-2-spirocyclohexane | 11.2 | 5 | 3 | 4 | 6 | 0 | 0 | 0 | 6 | 4 | 9 | 1 | 8 | 9 | 7 | 9 | 9 | 9 | 6 | 4 | 0 |
| | 1.1 | | | | | | | | 0 | 0 | 5 | 0 | 6 | 0 | 0 | 8 | 9 | 9 | 6 | 5 | 1 | — |
| 4-benzyloxymethyl-2-benzyl-2,4-dimethyl-1,3-dioxolane | 11.2 | 2 | 0 | 4 | 0 | 0 | 0 | 0 | 1 | 0 | 9 | 1 | 7 | 3 | 2 | 8 | 7 | 9 | 1 | 3 | 0 | 0 |
| | 1.1 | | | | | | | | 0 | — | 3 | 0 | 2 | 1 | 0 | 3 | 1 | 9 | 0 | 0 | — | — |
| 4-benzyloxymethyl-4-methyl-1,3-dioxolane-2-spirocyclopentane | 11.2 | 6 | 4 | 7 | 0 | 0 | 0 | 0 | 5 | 5 | 9 | 4 | 8 | 9 | 9 | 9 | 9 | 9 | 9 | 6 | 4 | 0 |
| | 1.1 | | | | | | | | 0 | 0 | 7 | 0 | 4 | 0 | 0 | 9 | 9 | 0 | 2 | 0 | — |
| 4-benzyloxymethyl-4-methyl-1,3-dioxolane | 11.2 | 5 | 2 | 6 | 1 | 4 | 0 | 2 | 1 | 4 | 2 | 1 | 3 | 5 | 3 | 1 | 7 | 9 | 7 | 5 | 3 | 0 |
| | 1.1 | | | | | | | | 0 | 0 | 0 | 0 | 0 | 0 | 0 | 0 | 0 | 8 | 0 | 0 | 0 | — |
| 4-benzyloxymethyl-2,4-dimethyl-1,3-dioxolane | 11.2 | 6 | 2 | 6 | 2 | 0 | 0 | 0 | 1 | 5 | 6 | 1 | 7 | 8 | 5 | 5 | 9 | 9 | 8 | 4 | 2 | 0 |
| | 1.1 | | | | | | | | | | | | | | | 0 | 0 | 8 | 4 | 0 | 0 | — |
| 4-phenoxymethyl-4-methyl-2-phenyl-1,3-dioxolane | 11.2 | 0 | 0 | 4 | 0 | 0 | 0 | 0 | 2 | 2 | 7 | 1 | 7 | 8 | 3 | 5 | 9 | 9 | 0 | 1 | 0 | 0 |
| | 1.1 | | | | | | | | 0 | 0 | 0 | 0 | 0 | 3 | 0 | 0 | 3 | 9 | — | 0 | — | — |
| 4-benzyloxymethyl-4-methyl-2-(2-phenylethyl)-1,3-dioxolane | 11.2 | 7 | 4 | 7 | 1 | 4 | 1 | 0 | 3 | 0 | 8 | 2 | 7 | 6 | 5 | 9 | 9 | 9 | 6 | 6 | 1 | 0 |
| | 1.1 | | | | | | | | 0 | — | 6 | 1 | 5 | 3 | 0 | 4 | 9 | 9 | 2 | 2 | 0 | — |
| 4-benzyloxymethyl-4-methyl-1,3-dioxolane-2-spirocyclopentane | 11.2 | 6 | 4 | 7 | 0 | 0 | 1 | 0 | 5 | 1 | 7 | 1 | 8 | 6 | 5 | 9 | 7 | 9 | 1 | 5 | 1 | 0 |
| | 1.1 | | | | | | | | 0 | 0 | 1 | 0 | 0 | 0 | 0 | 2 | 7 | 9 | 1 | 0 | 0 | 0 |

EXAMPLE XI

Fungicidal Activity

The fungicidal activity of the compounds of the invention was tested as follows:

Intact leaves or leaf pieces of vine, potato and wheat were supported on water-saturated seed germination pads in 9 cm petri dishes and were sprayed with aqueous suspensions containing 1000 ppm of the test compound. The leaves or leaf pieces were allowed to dry and were then inoculated with spores of *Plasmopara viticola* (vine downy mildew), *Phytophthora infestans* (potato late blight) and *Puccina recondita* (brown wheat rust), respectively. Observations on the development of disease symptoms were made after 2–7 days.

The results of the tests are shown in Table 5 in which a result 2 indicates more than 80% control of the fungal disease, a result 1 indicates 50–80% control and a result 0 indicates less than 50% control.

We claim as our invention:

1. A method for controlling weeds which comprises applying to the weed habitat a herbicidally effective amount of a compound of the formula

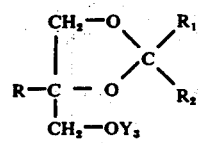

wherein R is an alkyl group of 1 to 6 carbon atoms; $R_1$ and $R_2$ each is hydrogen, a lower alkyl group, a lower alkyl group substituted by phenyl or a phenyl group optionally substituted by chlorine or by an alkyl group, or $R_1$ and $R_2$ together may be a polymethylene group of 3 to 6 carbon atoms; and $Y_3$ is a phenyl group, a chlorophenyl group, or benzyl optionally substituted on the Table 5

| Compound | Fungicidal Activity | | |
|---|---|---|---|
| | P.viticola | P.infestans | P.recondita |
| 4-benzyloxymethyl-2,2,4-trimethyl-1,3-dioxolane | 1 | 0 | 0 |
| 4-benzyloxymethyl-4-methyl-2-phenyl-1,3-dioxolane | 2 | 2 | 0 |
| 4-benzyloxymethyl-4-methyl-1,3-dioxolane-2-spirocyclohexane | 2 | 2 | 0 |
| 4-benzyloxymethyl-4-methyl-1,3-dioxolane-2-spirocyclopentane | 0 | 1 | 0 | ring by from 1 to 3 atoms of chlorine or fluorine or by a lower alkyl group or by a phenyl group.

2. A method as claimed in claim 1 wherein R is methyl or ethyl; $R_1$ and $R_2$ each is methyl or hydrogen and $Y_3$ is benzyl optionally substituted by from 1 to 3 chlorine atoms.

3. A method for controlling weeds which comprises applying to the weed habitat a herbicidally effective amount of a compound of the formula

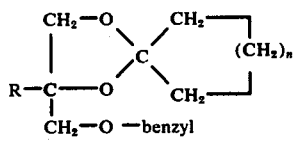

wherein R is alkyl of 1 to 6 carbon atoms and n is 2, 3 or 4.

4. A method according to claim 2 wherein R and $R_1$ are methyl, $R_2$ is hydrogen and $Y_3$ is benzyl optionally substituted by from 1 to 3 chlorine atoms.

5. A method according to claim 2 wherein R is ethyl, $R_1$ and $R_2$ are methyl and $Y_3$ is benzyl optionally substituted by 1 to 3 chlorine atoms.

6. A method according to claim 3 wherein R is methyl.

7. A herbicidal formulation comprising a compound as described in claim 1 together with an adjuvant therefor.

* * * * *